United States Patent [19]
Yamamoto et al.

[11] Patent Number: 5,741,355
[45] Date of Patent: Apr. 21, 1998

[54] PEARLESCENT PIGMENT, AND PAINT COMPOSITION, COSMETIC MATERIAL, INK AND PLASTICS BLENDED WITH THE NEW PEARLESCENT PIGMENT

[75] Inventors: Masaru Yamamoto; Akitsugu Ando; Tetsushi Kosugi, all of Toyohashi, Japan

[73] Assignee: Topy Industries, Limited, Tokyo, Japan

[21] Appl. No.: 582,427

[22] Filed: Jan. 3, 1996

[30] Foreign Application Priority Data

| Jan. 27, 1995 | [JP] | Japan | 7-030182 |
| Jan. 27, 1995 | [JP] | Japan | 7-030188 |
| Mar. 31, 1995 | [JP] | Japan | 7-097520 |

[51] Int. Cl.⁶ ............................................. C04B 14/20
[52] U.S. Cl. ............................................. 106/417; 106/419
[58] Field of Search ............................................. 106/417, 418

[56] References Cited

U.S. PATENT DOCUMENTS

| 4,883,539 | 11/1989 | Mattila et al. | 106/417 |
| 5,094,852 | 3/1992 | Ohno et al. | 424/401 |
| 5,433,779 | 7/1995 | DeLuca, Jr. | 106/418 |

FOREIGN PATENT DOCUMENTS

| 0 287 354 A1 | 10/1988 | European Pat. Off. |
| A-06 093 205 | 4/1994 | Japan. |
| A-06 240 172 | 8/1994 | Japan. |
| A-07 258 031 | 9/1995 | Japan. |

*Primary Examiner*—Deborah Jones
*Attorney, Agent, or Firm*—Armstrong, Westerman, Hattori, McLeland & Naughton

[57] ABSTRACT

The present invention provides a pearlescent pigment, which solves the problems such as development of yellow color at mass tone angle or shade side and non-clearness of interference colors. The pearlescent pigment coated with a metal oxide on a synthetic mica of the present invention is characterized in that said synthetic mica has average refractive index of not more than 1.58, surface of synthetic mica particles is smoothened and made flaky, and iron content in the synthetic mica is not higher than 1.0%.

24 Claims, 1 Drawing Sheet

PEARLESCENT PIGMENT, AND PAINT COMPOSITION, COSMETIC MATERIAL, INK AND PLASTICS BLENDED WITH THE NEW PEARLESCENT PIGMENT

BACKGROUND OF THE INVENTION

The present invention relates to a pearlescent pigment produced with a synthetic mica as a base material and also to a paint composition, cosmetic material, ink and plastics containing said pearlescent pigment.

In the past, a pearlescent pigment has been known, which shows pearl-like luster and is produced by coating a metal oxide such as iron oxide, titanium oxide, etc. on a natural mica. This conventional type pearlescent pigment is disadvantageous in that it develops yellow color specific to mica at mass tone angle or shade side, and that interference effect is weak, and hence interference colors are not clear.

On the other hand, a synthetic mica provides flaky particles, and it can be used as a base material for pearlescent pigment in this respect. However, the pearlescent pigment using synthetic mica of the known type has problems in that it exhibits yellow color at mass tone angle or shade side and interference colors are not clear just as in the case where natural mica is used.

Because synthetic mica has a hard crystal and is not easily cleaved, it cannot be turned into flaky particle with a smooth surface by normal procedure, and rather it is turned to powder of an undefined shape having rugged cross-sections and surfaces. Thus, it cannot be used as the base material for pearlescent pigment on which thin layer of titanium oxide and the like are to be coated. This is also described in Japanese Patent Publication No.24930 of 1972.

The present applicant has developed a pearlescent pigment which shows pearl-like luster by processing synthetic mica powder in a heat treatment at 600° to 1350° C. to smoothen the surfaces and by coating fine particles of metal oxide on the surface, and a patent application has been already filed in Japan. However, this pearlescent pigment is disadvantageous in that mica powder tightly aggregates with each other and this impairs the luster, which is very important as a pearlescent pigment.

It can be identified by pearl parameter whether the synthetic mica used as base material is flaky with a smooth surface or not.

The pearl parameter is expressed by: specific volume (A)×powder luster value (B). In the past, no synthetic mica having pearl parameter of more than 8 has been known. This is because the conventional type synthetic mica has a harder crystal and cannot be turned into flaky particles with a smooth surface compared with natural mica, and also because, when it is smoothed and processed through the heat treatment, the luster will be impaired.

SUMMARY OF THE INVENTION

It is an object of the present invention to provide a pearlescent pigment having a synthetic mica as a base material, by which it is possible to solve the problems such as development of yellow color at mass tone angle or shade side or non-clearness of interference colors.

It is another object of the present invention to provide a pearlescent pigment having a synthetic mica as a base material, by which it is possible to provide superb brightness.

It is still another object of the present invention to provide a pearlescent pigment using a synthetic mica, which has smoothed surface without heat treatment and having pearl parameter of more than 10.

The present inventors have fervently studied for solving the above problems and successfuly synthesized a synthetic mica containing iron components by not more than 1.0%, or more preferably by not more than 0.1%, trying to prevent intermingling of iron components in the synthetic mica in raw material and manufacturing process. When a pearlescent pigment was produced with this synthetic mica as base material, it was found that the pigment did not develop yellow color at mass tone angle or shade side and non-clearness of interference colors was not found.

Specifically, the pearlescent pigment according to the present invention comprises a synthetic mica coated with a metal oxide on it, whereby average refractive index of the synthetic mica is 1.58 or less, surface of synthetic mica particles is smoothened and made flaky, and iron content in the synthetic mica is not higher than 1.0%.

The above and other objects and advantages of the invention will become more apparent from the following description.

DETAILED DESCRIPTION OF THE PREFERRED EMBODIMENTS

Figure 1:
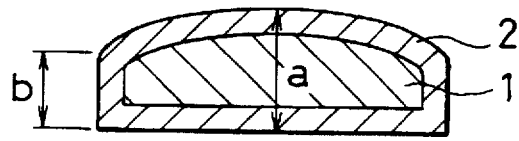
FIG. 1 is a schematical enlarged cross-sectional view of a preferred embodiment of a pearlescent pigment of the present invention.
Figure 2:
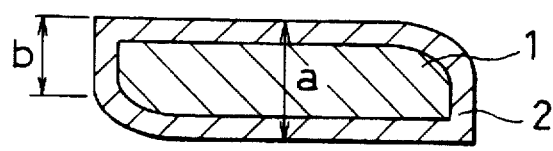
FIG. 2 is a schematical enlarged cross-sectional view of another preferred embodiment of a pearlescent pigment of the present invention.
Figure 3:
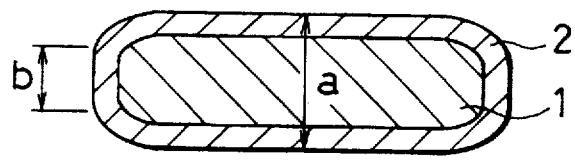
FIG. 3 is a schematical enlarged cross-sectional view of a still another embodiment of the pearlescent pigment of the present invention.
Figure 4:
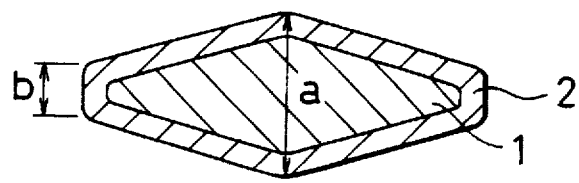
FIG. 4 is a schematical enlarged cross-sectional view of a yet another embodiment of the pearlescent pigment of the present invention.

The synthetic mica used in the present invention is expressed by the following general formula:

$$X_{0.5-1}Y_{2-3}Z_4O_{10}(F,OH)_2 \qquad (1)$$

where X is an interlayer ion occupying coordination number of 12 and represents $K^+$, $Na^+$, $Li^+$, $Rb^+$, $Cs^+$, $Tl^+$, $Ca^{2+}$, $Sr^{2+}$ and $Ba^{2+}$.

Y is an octahedral ion occupying coordination number of 6 and represents $Mg^{2+}$, $Fe^{2+}$, $Co^{2+}$, $Ni^{2+}$, $Mn^{2+}$, $Li^+$, $Ti^{2+}$, $Zn^{2+}$, $Cu^{2+}$, $Al^{3+}$, $Ti^{3+}$, $Cr^{3+}$, $Fe^{3+}$ and $Mn^{3+}$.

Z is a tetrahedral ion occupying coordination number of 4 and represents $Si^{4+}$, $Al^{3+}$, $B^{3+}$, $Fe^{3+}$, $Mn^{3+}$, $Be^{2+}$, $Zn^{2+}$ and $Ge^{4+}$.

As the synthetic mica used in the present invention, fluorine mica such as fluoro phlogopite, fluoro tetrasilicic mica, fluoro taeniolite and isomorphous substituent of these substances can be used preferably. In particular, it is preferable to use fluoro phlogopite.

Among the above synthetic mica, it may be used a synthetic mica, which contains at least one type selected from Ti, Zn, Na, B, Li, Ca, Ge, Sr and Zr by 0.01 to 5%.

The method to produce synthetic mica may be synthesis by melting, hydrothermal synthesis, solid phase reaction, etc. In particular, it is preferable to use synthesis by melting because crystallinity is good.

As the synthesis by melting method, an internal resistance electric melting method an external resistance electric melting method are known. In the industrial application, the internal resistance electric melting method with higher production efficiency is adopted.

In the conventional internal resistance electric melting method, raw material of synthetic mica is melted first, and a perforation is bored in the shell. Then, melted substance is taken out in frame. However, only synthetic mica having lower crystallinity can be obtained by this conventional method.

It is preferable that the raw material synthetic mica used in the present invention is a mica having good crystallinity. To obtain the mica having such good crystallinity, it is necessary to melt the raw material synthetic mica by the internal resistance electric melting method. Then, a perforation is bored in the shell, and the melted substance taken out through the hole is in a heat insulating case.

There is no specific restriction to shape and material of the heat insulating case as far as it can receive the melted substance and it has heat insulating property.

The synthetic mica produced by the above procedure has good crystallinity, and synthetic mica powder having a high aspect ratio can be produced.

The synthetic mica used in the present invention must contain iron components by not more than 1.0%, or more preferably by not more than 0.1%. If the iron content is more than these values, problems occur such as development of yellow color at mass tone angle or shade side, or non-clearness of interference colors. In particular, in case iron content is not more than 0.1%, no problem occurs such as development of yellow color at mass tone angle or shade side, or non-clearness of interference colors. Luminance also increases.

According to the literature, conventional type synthetic mica contains iron components by 0.01 mol or more (converted to Fe: 0.13%).

The synthetic mica of the present invention, in which total iron content is not more than 1.0%, or more preferably not more than 0.1%, can be produced as follows:

Raw materials of synthetic mica, i.e. $SiO_2$, $MgO$, $Al_2O_3$, $K_2SiF_6$, $KF$ and talc, feldspar, etc. are selected or purified in such manner that total iron content in the impurities contained in the raw materials is not more than 1.0%, or more preferably not more than 0.1%.

To prevent intermingling of Fe from the mixer, etc. when the raw materials are mixed, a mixer etc. coated with ceramics must be used.

Further, iron components possibly intermingled in mixing and pulverizing processes should be removed if necessary by means of an iron-removing device after pulverizing or by means of agents such as an inorganic acid, organic acid, chelating agent, etc.

The synthetic mica powder used in the present invention must have smooth surface. Because synthetic mica has hard crystal and is difficult to cleave, it cannot be turned into flaky pieces with a smooth surface by normal procedures, and it is turned into powder having indefinite shape with rugged cross-section or surface.

To produce synthetic mica powder with a smooth surface, it is recommended to pulverize easily flakable mass of synthetic mica, or the melted substance as taken out through the perforation of the shell as described above is crystallized in the heat insulating case and pulverized.

To obtain the easily flakable mass of synthetic mica, it is recommended, for example, that fine powder of synthetic mica is added by at least 1% or more to the melt of synthetic mica during synthesis by melting of synthetic mica and is solidified and crystallized. Such crystallized mass of synthetic mica can be easily flaked. Even when it is crushed by an ordinary crusher such as a jaw crusher, roughening and damaging of mica surface can be avoided.

In case the plate-like synthetic mica is further pulverized to particle size of 100 microns or smaller using hammer mill, roll mill, ball mill, etc., excessive crushing force is applied on mica particles, thus resulting in powder having indefinite shape with rugged cross-sections and surfaces. To solve this problem, a high viscosity medium such as glycerine, liquid paraffin, ethyleneglycol, etc. may be added to pulverize mica without roughening the surface. Or, mica can be pulverized without roughening mica surface by cleaving it under water pressure. By pulverizing mica without roughening mica surface, it is possible to produce synthetic mica having pearl parameter of more than 10.

When pulverizing, special care should be taken not to apply excessive pulverizing force in order to have a larger average particle size. In this way, a pearl parameter of about 30 can be attained.

In the present invention, synthetic mica may be processed by heat treatment at 600° to 1350° C. to have smooth mica surface.

The synthetic mica used in the present invention has refractive index of not more than 1.58. The use of this synthetic mica makes it possible to increase the luminance of the pearlescent pigment, to provide sharp and bright color and to exclude blurred complementary colors. This may be attributable to the fact that the difference of refractive index of mica from that of the oxide coated on it is increased or that the difference of refractive index of the synthetic mica from that of the organic resin (refractive index: 1.4 to 1.6), to which the pearlescent pigment of the present invention is applied, is decreased. However, the reasons are theoretically not elucidated yet.

It is preferable that flaky particles having diameter of plane direction of 3 to 100 μm and thickness of 0.05 to 1 μm are used as the synthetic mica used in the present invention. By the use of such a synthetic mica, it is possible to increase luminance of the pearlescent pigment, to provide sharp and bright color, and to exclude blurred complementary colors.

It is preferable that aspect ratio of the synthetic mica is 60 or more. If it is lower than 60, interference effect is not sufficient, and it is difficult to provide good luster.

As the pearlescent pigment of the present invention, it is preferable to use the pigment having particles with thickness thinner at end surface than at the center. The thickness may be gradually thinned from the center or it may be suddenly thinned near the end surface.

The ratio of the thickness at the end surface to the thickness at the center is preferably not more than 0.9. If it is higher than 0.9, sufficient effect cannot be obtained.

Figure 5:
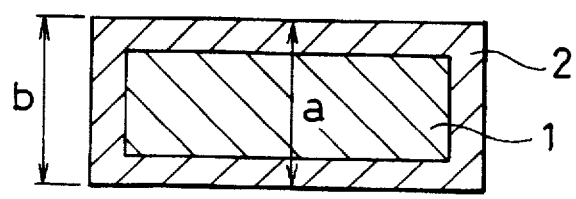
FIG. 5 is a schematical enlarged cross-sectional view of a conventional type pearlescent pigment.

FIG. 1 to FIG. 4 each represents a schematical enlarged cross-sectional view of the pearlescent pigment of the present invention, which comprises a synthetic mica 1 coated with a metal oxide 2. FIG. 5 is an enlarged cross-sectional view of a conventional type pearlescent pigment.

In the pearlescent pigment of the present invention shown in FIG. 1 to FIG. 4, the thickness "a" at the center is larger than the thickness "b" at the end surface. In the pearlescent pigment shown in FIG. 5, i.e. in the conventional synthetic mica 1 coated with a metal oxide 2, the thickness "a" at the center and the thickness "b" at the end are approximately equal to each other.

To have the center thickness "a" larger than the end thickness "b" in the pearlescent pigment, the center thickness of the raw material synthetic mica must be larger than the end thickness. This is because the coating layer of the metal oxide 2 is very thin and it is technically difficult to provide large thickness difference by the coating layer.

To have the end thickness thinner than the center thickness in flaky synthetic mica, surface pulverizing method by fluidized bed jet mill may be used. It is assumed that the end portion is worn out more by intense collision of mica particles than at the center and the end thickness is made thinner than the center thickness. Of course, the end portion may be thinned by other means or methods.

To coat the metal oxide on the synthetic mica powder, any method already known may be used. To coat titanium oxide, synthetic mica powder is suspended in dilute aqueous solution of titanic acid and this is heated to 70° to 100° C. Then, titanate is hydrolyzed, and hydrate titanium oxide particles are deposited on the synthetic mica powder, which is then calcined at high temperature of 700° to 1000° C. As the metal oxide used, for example, oxides of titanium, zirconium, iron, chromium or vanadium may be used. These may be used alone or in mixture.

The metal oxide, in particular, titanium dioxide, is preferably rutilized by a rutilizing agent such as tin chloride. By the rutilization, the weatherproof property of the pearlescent pigment can be improved.

Further, titanium oxide on the surface of the synthetic mica may be turned into reductive titanium oxide by a known method to produce colored pearlescent pigment.

To improve the weatherproof property of the pearlescent pigment, the surface may be processed with alumina, silica, or titania, or with a chromium compound, or with a hydrated zirconium compound, or with a polysiloxane and rare earth element compound or any other known method.

The pearlescent pigment of the present invention can be used in the same manner as the conventional pearlescent pigment, i.e. it can used as a paint composition by mixing in any type of paint, or as a plastic material exhibiting unique pearl-like appearance by mixing in various types of plastics, or as a colorant for cosmetic products or for ink.

By the use of synthetic mica having Fe content of not more than 1.0%, or more preferably by not more than 0.1%, with smooth surface and flaky as base material, a pearlescent pigment can be obtained, which eliminates the problems such as development of yellow color at mass tone angle or shade side or non-clear interference colors. However, the reasons are theoretically not completely elucidated yet.

By limiting Fe content of synthetic mica to not more than 1.0%, or more preferably to not more than 0.1%, and by making the end thickness thinner than the center thickness, the pearlescent pigment having superb effects as not known in the past can be obtained, while the reasons for such improvement are not completely elucidated. The possible causes may be as follows: By making the end thickness thinner than the center thickness, the influence of irregular reflection at the end surface can be avoided. The effect of iron component such as light absorption can be virtually eliminated. By cumulative effect of these actions, it may be possible to obtain a pearlescent pigment, which has high luminance to develop sharp and bright color, or to exclude blurred complementary colors. Further, the mica surface is smoothed without heat treatment, and this may be helpful to avoid aggregation of the mica powder to obtain a synthetic mica having pearl parameter of more than 10, and to improve the glossiness of the pearlescent pigment. Thus, the use of this synthetic mica may contribute to high glossiness and good luminance of the pigment.

In the following, description will be given on the features of the present invention referring to examples and comparative examples, while it is needless to say that the present invention is not limited to these examples.

(EXAMPLE 1)

About 200 kg of raw materials, which contains about 40 parts of silicic acid anhydride, about 30 parts of magnesium oxide, about 13 parts of aluminum oxide, and about 17 parts of potassium silicofluoride in weight ratio, were placed in a melting furnace, and the furnace was energized for about 2 hours to produce a melted substance. A perforation was bored into the shell from the outlet, and the melted substance was allowed to flow out of the furnace and was received in a heat insulating case, which is made of heat insulating bricks with the outer surfaces lined with ceramic boards. After being cooled, the size of the synthetic mica crystal thus obtained was 7 cm.

The crystals obtained above were pulverized by a hammer mill to prepare synthetic fluoro phlogopite powder.

Into a glass container with volume of 1 liter, 20 g of synthetic fluoro phologopite having particle size of 10 to 60 μm (average refractive index 1.56; Fe content 0.04%) and 400 ml of water were placed and stirred up. Next, 200 ml of titanyl sulfate solution ($TiO_2$ 80 g/liter) was added, and this was heated quickly up to 100° C. and was allowed to react for 3 hours at this temperature. After the completion of the reaction, it was filtered, washed with water and dried at 110° C. The powder thus prepared was calcined at 800° C. for one hour, and the pearlescent pigment of the present invention was obtained. When this pearlescent pigment was dispersed in clear lacquer, golden color developed, showing reflection with satisfactory glossiness. The color tone at mass tone angle or shade side and non-clearness of interference colors of this pearlescent pigment were determined. The results are shown in Table 1.

(Testing Method)

To determine the color tone at mass tone angle or shade side, a paint containing the pearlescent pigment was coated on a white panel and was dried. The surface of the coated film was observed from an angle to exclude interference colors, and the development of yellow color was evaluated according to the following three ratings;

◎ . . . No development of yellow color was observed.

○ . . . Yellow color developed very slightly.

X . . . Yellow color developed to considerable extent.

To determine the non-clearness of interference colors, a paint containing the pearlescent pigment was coated on a white or black panel and was dried, and interference colors on the coated surface were examined. The non-clearness of the interference colors was evaluated according to the following three ratings;

◎ . . . Non-clearness was not observed.

○ . . . Non-clearness was observed very slightly.

X . . . Non-clearness was noted to considerable extent.

(EXAMPLE 2)

Into a glass container with volume of 1 liter, 25 g of boron-containing fluoro phlogopite with particle size of 10 to 60 μm (average refractive index 1.52; Fe content 0.05%) and 400 ml of water were placed and stirred up. Next, 200 ml of titanyl sulfate solution ($TiO_2$ 80 g/liter) was added, and it was heated quickly up to 100° C. and was allowed to react for 3 hours at this temperature. After the completion of the reaction, it was filtered, washed with water and was dried at 110° C. Total quantity of the dried substance was transferred to a glass container, and 570 ml of water was added, and it was stirred up. To this, 30 ml of zirconium sulfate solution (ZrO$_2$=100 g/liter) was added, and urea was further added gradually to have pH value of 2.0. This solution was quickly heated up to 100° C., and the reaction was continued for one hour. At the completion of the reaction, it was filtered, washed with water and dried at 110° C. After calcining this at 800° C., the pearlescent pigment of the present invention was obtained. When this pearlescent pigment was dispersed in clear lacquer, bright golden color developed. By the same procedure as in Example 1, the color tone at mass tone angle or shade side as well as non-clearness of the interference colors were determined. The results are shown in Table 1.

(EXAMPLE 3)

Into a glass container with volume of 1 liter, 30 g of the same synthetic fluoro phlogopite as used in Example 1 and 400 ml of water were placed and stirred up. Next, 200 ml of zirconium sulfate solution (ZrO$_2$=100 g/liter) was added, and urea was further added gradually to have pH value of 2.0. This solution was heated quickly up to 100° C., and the reaction was continued for 3 hours. After the completion of the reaction, it was filtered, washed with water and was dried at 110° C. This was then calcined at 800° C. for one hour, and the pearlescent pigment of the present invention was obtained. When this pearlescent pigment was dispersed in clear lacquer, silvery white color with yellow tone external appearance developed, and reflection with satisfactory glossiness was noted. By the same procedure as in Example 1, the color tone at mass tone angle or shade side as well as non-clearness of the interference colors of this pearlescent pigment were determined. The results are summarized in Table 1.

(EXAMPLE 4)

Into a glass container with volume of 1 liter, 25 g of sodium-containing synthetic fluoro phlogopite powder having particle size of 10 to 60 μm (average refractive index 1.53; Fe content 0.10%) and 370 ml of water were placed and stirred up. Next, 30 ml of chromic sulfate solution (Cr$_2$O$_3$=100 g/liter) was added, and this was heated up to 90° C. Further, 200 ml of titanyl sulfate solution (TiO$_2$ 80 g/liter) was added, and it was heated up to 100° C., and the reaction was continued for 3 hours. After the completion of the reaction, it was filtered, washed with water and was dried at about 110° C. Then, it was calcined at 800° C. for one hour, and the pearlescent pigment of the present invention was obtained. This pearlescent pigment developed bright golden reflection color. By the same procedure as in Example 1, the color tone at mass tone angle or shade side as well as non-clearness of interference colors of this pearlescent pigment were determined. The results are shown in Table 1.

(EXAMPLE 5)

Using 30 g of the synthetic fluoro phlogopite used in Example 1, 45 g of synthetic mica coated with titanium dioxide was prepared by the same procedure as in Example 1. Total quantity of the synthetic mica thus prepared was transferred to a glass container, and 570 ml of water was added and it was stirred up. To this, 30 ml of ferric sulfate solution (Fe$_2$O$_3$=100 g/liter) was added, and urea was further added gradually to have pH value of 2.0. This solution was quickly heated up to 100° C., and the reaction was continued for one hour. After the completion of the reaction, it was filtered, washed with water and dried at 110° C. Then, it was calcined at 800° C. for one hour, and the pearlescent pigment of the present invention was obtained. When this pearlescent pigment was dispersed in clear lacquer, pearl-like gloss with dense golden reflection color developed and good interference property was obtained. By the same procedure as in Example 1, the color tone at mass tone angle or shade side as well as non-clearness of interference colors of the pearlescent pigment were determined. The results are shown in Table 1.

(EXAMPLE 6)

By the same procedure as in Example 1, mica coated with titanium dioxide was prepared except that synthetic fluoro phlogopite having particle size of 10 to 60 μm (average refreactive index 1.56; Fe content 1.0%) was used. When this was dispersed in clear lacquer, golden color developed, and reflection with satisfactory glossiness was noted. By the same procedure as in Example 1, the color tone at mass tone angle or shade side as well as non-clearness of interference colors of this pearlescent pigment were determined. The results are shown in Table 1.

(EXMAPLE 7)

Into a glass container with volume of 1 liter, 20 g of synthetic fluoro phlogopite containing Ti by 1% (average refractive index 1.56; Fe content 0.04%) and 400 ml of water were placed and stirred up. Next, 200 ml of titanyl sulfate solution (TiO$_2$ 80 g/liter) was added, and this was quickly heated up to 100° C., and the reaction was continued for 3 hours at this temperature. After the completion of the reaction, it was filtered, washed with water and was dried at 110° C. The powder thus prepared was calcined at 800° C. for one hour, and the pearlescent pigment of the present invention was obtained. When this pearlescent pigment was dispersed in clear lacquer, golden color developed, and reflection with satisfactory gloss was noted. The color tone at mass tone angle or shade side and non-clearness of the interference colors of this pearlescent pigment were determined. The results are shown in Table 1.

(EXAMPLES 8 TO 16)

The pearlescent pigment of the present invention was prepared by the same procedure as in Example 1, except that the following synthetic fluoro phlogopite powder was used:

Example 8: Synthetic fluoro phlogopite containing Zn by 1% (Fe content 0.06%)

Example 9: Synthetic fluoro phlogopite containing Ba by 1% (Fe content 0.04%)

Example 10: Synthetic fluoro phlogopite containing Na by 1% (Fe content 0.05%)

Example 11: Synthetic fluoro phlogopite containing B by 1% (Fe content 0.04%)

Example 12: Synthetic fluoro phlogopite containing Li by 1% (Fe content 0.04%)

Example 13: Synthetic fluoro phlogopite containing Ca by 1% (Fe content 0.07%)

Example 14: Synthetic fluoro phlogopite containing Ge by 1% (Fe content 0.04%)

Example 15: Synthetic fluoro phlogopite containing Sr by 1% (Fe content 0.84%)

Example 16: Synthetic fluoro phlogopite containing Zr by 1% (Fe content 0.04%)

When these were dispersed in clear lacquer, golden color developed, and reflection with satisfactory glossiness was noted. The color at mass tone angle or shade side and non-clearness of intereference colors of the pearlescent pigment were determined. The results are shown in Table 1.

(EXAMPLE 17)

To a glass container with volume of 1 liter, 25 g of synthetic fluoro phlogopite powder containing Zn by 1% (Fe content 0.05%) and 370 ml of water were placed and stirred up. Next, 30 ml of chromic sulfate solution ($Cr_2O_3$=100 g/liter) was added, and this was heated up to 90° C. Further, 200 ml of titanyl sulfate solution ($TiO_2$ 80 g/liter) was added and this was heated up to 100° C., and the reaction was continued for 3 hours. After the completion of the reaction, it was filtered, washed with water and was dried at 110° C. Then, it was calcined at 800° C. for one hour, and the pearlescent pigment of the present invention was obtained. This pearlescent pigment developed bright golden reflection color. By the same procedure as in Example 1, the color tone at mass tone angle or shade side and non-clearness of interference colors of this pearlescent pigment were determined. The results are shown in Table 1.

(EXAMPLE 18)

Into a glass container with volume of 1 liter, 20 g of synthetic fluoro phlogopite powder having average particle diameter of plane direction of 20 μm and average aspect ratio of 80 (Fe content 0.04%) and 400 ml of water were placed and stirred up. To this, 5 ml of tin chloride solution (converted to tin oxide: 5 weight % solution) was added, and this was allowed to react at 70° C. for 30 minutes.

Next, 200 ml of titanyl sulfate solution ($TiO_2$ 80 g/liter) was added, and this was quickly heated up to 100° C., and the reaction was continued for 3 hours at this temperature. After the completion of the reaction, it was filtered, washed with water and was dried at 110° C. The powder thus obtained was calcined at 800° C. for one hour, and the pearlescent pigment of the present invention was obtained. When crystal form of the layer coated with titanium oxide was identified by powder X-ray diffraction method, no diffraction peak based on anatase type crystal was found, and diffraction peak due to rutile type crystal was observed.

When this pearlescent pigment was dispersed in clear lacquer, golden color developed, and reflection with satisfactory glossiness was noted. The color tone at mass tone angle or shade side as well as non-clearness of interference colors of this pearlescent pigment were determined. The results are shown in Table 1.

(EXAMPLE 19)

Into a glass container with volume of 1 liter, 30 g of synthetic fluoro phlogopite powder (Fe content 0.05%) having average particle diameter of plane direction of 20 μm and average aspect ratio of 80 and 400 ml of water were placed and stirred up. Next, 200 ml of zirconium sulfate solution ($ZrO_2$=100 g/liter) was added, and urea was further added gradually to have pH value of 2.0. This solution was quickly heated up to 100° C., and the reaction was continued for 3 hours. After the completion of the reaction, it was filtered, washed with water and was dried at 110° C. Then, it was calcined at 900° C. for one hour, and the pearlescent pigment of the present invention was obtained. When this pearlescent pigment was dispersed in clear lacquer, silvery white color with yellow tone external appearance developed, and reflection with satisfactory glossiness was noted. By the same procedure as in Example 1, the color tone at mass tone angle or shade side as well as non-clearness of this pearlescent pigment were determined. The results are shown in Table 1.

(EXAMPLE 20)

Into a glass container with volume of 1 liter, 25 g of synthetic fluoro phlogopite powder having average particle diameter of plane direction of 30 μm and average aspect ratio of 100 (Fe content 0.05%) and 370 ml of water were placed and stirred up. Next, 30 ml of chromic sulfate solution ($Cr_2O_3$=100 g/liter) was added, and this was heated up to 90° C.

Further, 200 ml of titanyl sulfate solution ($TiO_2$ 80 g/liter) was added, and this was heated up to 100° C., and the reaction was ocntinued for 3 hours. After the completion of the reaction, it was filtered, washed with water and was dried at about 110° C. This was then calcined at 700° C. for one hour, and the pearlescent pigment of the present invention was obtained. This pearlescent pigment showed clear bluish reflection color. By the same procedure as in Example 1, the color tone at mass tone angle or shade side as well as the non-clearness of the interference colors of this pearlescent pigment were determined. The results are shown in Table 1.

(COMPARATIVE EXAMPLE 1)

A mica coated with titanium dioxide was prepared by the same procedure as in Example 1 except that natural muscovite powder (Fe content 1.2%; average refractive index 1.60) was used. When this was dispersed in clear lacquer, golden pearl-like gloss was noted, while width of interference zone was narrower, complementary colors were blurred, and color development was not distinct. By the same procedure as in Example 1, the color at mass tone angle or shade side as well as non-clearness of interference colors of this pearlescent pigment were determined. The results are shown in Table 1.

(COMPARATIVE EXAMPLE 2)

A mica coated with zirconium dioxide was prepared by the same procedure as in Example 3, except that natural muscovite powder (Fe content 1.1%; average refractive index 1.60) was used. When this was dispersed in clear lacquer, pearl-like gloss with silvery white tone was noted, while color width of interference zone was narrower compared with the pigment of the present invention prepared in Example 1, complementary colors were blurred, and color lacked distinctness. By the same procedure as in Example 1, the color tone at mass tone angle or shade side as well as non-clearness of the interference colors were determined. The results are shown in Table 1.

TABLE 1

| Example No. | Raw material mica | Inter-ference colors | Fe content (%) | yellow color at mass tone angle or shade side | Non-clearness |
|---|---|---|---|---|---|
| Example 1 | Synthetic fluoro phlogopite | Golden | 0.04 | ⊚ | ⊚ |
| Example 2 | B-containing synthetic fluoro phlogopite | Golden | 0.05 | ⊚ | ⊚ |
| Example 3 | Synthetic fluoro phlogopite | Silver | 0.04 | ⊚ | ⊚ |
| Example 4 | Na-containing synthetic fluoro phlogopite | Golden | 0.10 | ⊚ | ⊚ |
| Example 5 | Synthetic fluoro phlogopite | Golden | 0.04 | ⊚ | ⊚ |
| Example | Synthetic fluoro | Golden | 1.0 | ○ | ○ |

TABLE 1-continued

| Example No. | Raw material mica | Interference colors | Fe content (%) | yellow color at mass tone angle or shade side | Non-clearness |
|---|---|---|---|---|---|
| Example 6 | phlogopite | Golden | 0.04 | ⊚ | ⊚ |
| Example 7 | Ti-containing synthetic fluoro phlogopite | Golden | 0.06 | ⊚ | ⊚ |
| Example 8 | Zn-containing synthetic fluoro phlogopite | Golden | 0.04 | ⊚ | ⊚ |
| Example 9 | Ba-containing synthetic fluoro phlogopite | Golden | 0.05 | ⊚ | ⊚ |
| Example 10 | Na-containing synthetic fluoro phlogopite | Golden | 0.04 | ⊚ | ⊚ |
| Example 11 | B-containing synthetic fluoro phlogopite | Golden | 0.04 | ⊚ | ⊚ |
| Example 12 | Li-containing synthetic fluoro phlogopite | Golden | 0.07 | ⊚ | ⊚ |
| Example 13 | Ca-containing synthetic fluoro phlogopite | Golden | 0.04 | ⊚ | ⊚ |
| Example 14 | Ge-containing synthetic fluoro phlogopite | Golden | 0.84 | ○ | ○ |
| Example 15 | Sr-containing synthetic fluoro phlogopite | Golden | 0.04 | ⊚ | ⊚ |
| Example 16 | Zr-containing synthetic fluoro phlogopite | Golden | 0.05 | ⊚ | ⊚ |
| Example 17 | Zn-containing synthetic fluoro phlogopite | Golden | 0.04 | ⊚ | ⊚ |
| Example 18 | Synthetic fluoro phlogopite | Golden | 0.05 | ⊚ | ⊚ |
| Example 19 | Synthetic fluoro phlogopite | Silver | 0.05 | ⊚ | ⊚ |
| Example 20 | Synthetic fluoro phlogopite | Blue | 1.2 | X | X |
| Comparative example 1 | Natural muscovite | Golden | 1.1 | X | X |
| Comparative example 2 | Natural muscovite | Silver | | | |

(EXAMPLE 21)

Into a glass container with volume of 1 liter, 20 g of synthetic fluoro phlogopite powder pulverized to particles having particle size of 10 to 60 μm and a ratio of end thickness to center thickness of 0.7 and 400 ml of water were placed and stirred up. Next, 200 ml of titanyl sulfate solution (TiO₂ 80 g/liter) was added, and this was quickly heated up to 100° C., and the reaction was continued for 3 hours at this temperature. After the completion of the reaction, it was filtered, washed with water and was dried at about 110° C. The powder thus obtained was calcined at 800° C. for one hour, and the pearlescent pigment of the present invention was obtained. When this pearlescent pigment was dispersed in clear lacquer, golden color developed, and reflection with very high glossiness was noted. The glossiness (brightness), color clearness and blurred complementary colors of this pearlescent pigment were determined. The results are shown in Table 2.

(Testing Method)

(Glossiness)

To 1 g of thinner and 3 g of clear lacquer, 0.3 g of pearlescent pigment was mixed, and the mixture was dispersed well in an agate mortar. This was transferred to a piece of contrast chart (JIS K 5400) and was uniformly coated using an applicator (Taiyu Kizai Co., Ltd.; 100 μm deep). After drying this at room temperature, regular reflection ratio at 60° (glossiness) was determined by a gloss sensor (Nippon Denshoku Co., Ltd.; VG-2P).

(Color Clearness)

A specimen dispersed as described above was coated on a piece of measuring paper comprising a black portion and a white portion, using an applicator. The coated film on the black portion was observed by visual inspection, and color clearness was evaluated by the following ratings:

⊚ . . . Very clear

○ . . . Clear

X . . . Not clear (Blurred Complementary Colors)

○ . . . Not blurred

X . . . Blurred (EXAMPLE 22)

Into a glass container with volume of 1 liter, 25 g of synthetic fluoro phlogopite powder (Fe content 0.04%; average refractive index 1.56) pulverized to particles having particle size of 10 to 60 μm and the ratio of end thickness to center thickness of 0.8 were placed together with 400 ml of water and were stirred up. Next, 200 ml of titanyl sulfate solution (TiO₂ 80 g/liter) was added, and this was quickly heated up to 100° C., and the reaction was continued for 3 hours at this temperature. After the completion of the reaction, the solution was filtered, washed with water and was dried at about 110° C. Total quantity of this dried substance was transferred to a glass container, and this was stirred up by adding 570 ml of water. To this, 30 ml of zirconium sulfate solution (ZrO₂=100 g/liter) was added, and urea was further added gradually to have pH value of 2.0. This solution was quickly heated up to 100° C., and the reaction was continued for one hour. After the completion of the reaction, it was filtered, washed with water and was dried at 110° C. This was then calcined at 800° C. for one hour, and the pearlescent pigment of the present invention was obtained. When this pearlescent pigment was dispersed in clear lacquer, clear golden color developed, and reflection with very high glossiness was noted. By the same procedure as in Example 1, glossiness (brightness), color clearness, and blurred complementary colors of this pearlescent pigment were determined. The results are shown in Table 2.

(EXAMPLE 23)

Into a glass container having volume of 1 liter, 30 g of synthetic fluoro phlogopite powder (Fe content 0.04%; Average refractive index 1.56) pulverized to particles having particle size of 10 to 60 μm and the ratio of end thickness to center thickness of 0.9 were placed together with 400 ml of water and were stirred up. Next, 200 ml of zirconium sulfate solution (ZrO₂=100 g/liter) was added, and urea was further added gradually to have pH value of 2.0. This solution was heated quickly up to 100° C., and the reaction was continued for 3 hours. After the completion of the reaction, it was filtered, washed with water and was dried at 110° C. Then, it was calcined at 800° C. for one hour, and the pearlescent pigment of the present invention was obtained. When this pearlescent pigment was dispersed in clear lacquer, silvery white color with yellow tone developed, and reflection with very high glossiness was noted. By the same procedure as in Example 1, glossiness (brightness), color clearness, and blurred complementary colors of this pearlescent pigment were determined. The results are shown in Table 2.

(EXAMPLE 24)

Into a glass container having volume of 1 liter, 25 g of synthetic fluoro phlogopite powder (Fe content 0.04%; Average refractive index 1.56) pulverized to particles having particle size of 10 to 60 μm and a ratio of end thickness to center thickness of 0.6 were placed together with 370 ml of water and were stirred up. Then, 30 ml of chromic sulfate solution ($Cr_2O_3$=100 g/liter) was added, and this was heated up to 90° C. Further, 200 ml of titanyl sulfate solution ($TiO_2$ 80 g/liter) was added, and this was heated up to 100° C., and the reaction was continued for 3 hours. After the completion of the reaction, it was filtered, washed with water and was dried at 110° C. Then, it was calcined at 800° C. for one hour, and the pearlescent pigment of the present invention was obtained. This pearlescent pigment developed clear golden reflection color. By the same procedure as in Example 1, glossiness (brightness), color clearness and blurred complementary colors of this pearlescent pigment were determined. The results are shown in Table 2.

(EXAMPLE 25)

Using 30 g of synthetic fluoro phlogopite powder pulverized to particles having particle size of 10 to 60 μm and a ratio of end thickness to center thickness of 0.7 (Fe content 0.04%; Average refractive index 1.56), 45 g of synthetic mica coated with titanium dioxide was prepared by the same procedure as in Example 1. Total quantity of this substance was transferred to a glass container, and this was stirred up by adding 570 ml of water. To this, 30 ml of ferric sulfate solution ($Fe_2O_3$=100 g/liter) was added, and urea was gradually added to have pH value of 2.0. This solution was quickly heated up to 100° C., and the reaction was continued for one hour. After the completion of the reaction, it was filtered, washed with water and was dried at 110° C. Then, it was calcined at 800° C. for one hour, and the pearlescent pigment of the present invention was obtained. When this pearlescent pigment was dispersed in clear lacquer, dense golden reflection color developed, and pearl-like gloss with superb interference property was noted. By the same procedure as in Example 1, glossiness (brightness), color clearness and blurred complementary colors of this pearlescent pigment were determined. The results are shown in Table 2.

(EXAMPLE 26)

Into a glass container having volume of 1 liter, 20 g of synthetic fluoro phlogopite powder (Fe content 0.04%; Average refractive index 1.56) pulverized to particles having average particle diameter of plane direction of 20 μm and average aspect ratio of 80, and a ratio of end thickness to center thickness of 0.7 were placed together with 400 ml of water and were stirred up.

To this, 5 ml of tin chloride solution (converted to tin chloride: 5 weight % solution) was added, and this was allowed to react at 70° C. for 30 minutes.

Next, 200 ml of titanyl sulfate solution ($TiO_2$ 80 g/liter) was added, and this was quickly heated up 100° C., and the reaction was continued for 3 hours at this temperature. After the completion of the reaction, it was filtered, washed with water, and was dried at 110° C. The powder thus obtained was calcined at 800° C. for one hour, and the pearlescent pigment of the present invention was obtained. When the crystal form of the titanium dioxide layer was identified by powder X-ray diffraction method, no diffraction peak based on anatase type crystal was noted, and only diffraction peak due to rutile type crystal was observed.

When this pearlescent pigment was dispersed in clear lacquer, golden color developed, and reflection having very high glossiness was noted. The glossiness (brightness), color clearness and blurred complementary colors of this pearlescent pigment were determined. The results are shown in Table 2.

(COMPARATIVE EXAMPLE 3)

Synthetic mica coated with titanium dioxide was prepared by the same procedure as in Example 1 except that synthetic fluoro phlogopite powder (Fe content 1.0%) had approximately the same ratio of end thickness to center thickness as in Example 1. When this was dispersed in clear lacquer, golden color with pearl-like gloss was noted. Glossiness (brightness), color clearness and blurred complementary colors of the pearlescent pigment dispersed in the clear lacquer were determined. The results are shown in Table 2.

TABLE 2

| Example | Fe content (%) | End thickness/ center thickness | Color clearness | Blurred complementary colors | Glossiness |
| --- | --- | --- | --- | --- | --- |
| Example 21 | 0.04 | 0.7 | ⊚ | ○ | 90.2 |
| Example 22 | 0.04 | 0.8 | ⊚ | ○ | 84.5 |
| Example 23 | 0.04 | 0.9 | ⊚ | ○ | 86.1 |
| Example 24 | 0.04 | 0.6 | ○ | ○ | 84.2 |
| Example 25 | 0.04 | 0.7 | ○ | ○ | 85.3 |
| Example 26 | 0.04 | 0.7 | ⊚ | ○ | 90.6 |
| Comparative example 3 | 1.0 | 1.0 | X | X | 68.2 |

(EXAMPLES 27 TO 29)

To the melt of synthetic fluoro phlogopite produced by normal procedure, synthetic fluoro phlogopite powder was added by 3%, and this was solidified and crystallized, and an easily flakable mass of synthetic fluloro phlogopite was obtained. This was crushed using a hammer mill, and synthetic fluoro phlogopite powder having Fe content, average particle size, specific volume, powder glossiness and pearl parameter as shown in Table 3 was obtained. When crushing and pulverizing, special care should be taken not to apply excessive pulverizing force. In so doing, synthetic mica having higher pearl parameter can be obtained.

On the synthetic fluoro phlogopite powder thus obtained, titanium dioxide was coated by the same procedure as in Example 1, and the pearlescent pigment was obtained. The glossiness of the pearlescent pigment obtained was as shown in Table 3. For comparison purpose, synthetic fluoro phlogopite powder as prepared by conventional method was coated with titanium dioxide by the same procedure, and the pearlescent pigment was obtained. The glossiness of this pigment was determined, and the results are shown in Table 3.

TABLE 3

| | Fe content (%) | Average particle size *1 (μm) | Specific volume *2 (A) | Powder glossi- ness *3 (B) | Pearl para- meter (A) × (B) | Gloss- ness of pearles- cent pigment |
| --- | --- | --- | --- | --- | --- | --- |
| Example 27 | 0.04 | 10 | 1.5 | 6.5 | 10 | 86.2 |
| Example 28 | 0.04 | 20 | 1.9 | 6.5 | 12 | 89.0 |
| Example 29 | 0.04 | 50 | 1.9 | 8.0 | 15 | 90.3 |
| Compar- ative example 4 | 0.04 | 10 | 1.7 | 4.6 | 8 | 68.5 |
| Compar- ative example 5 | 0.04 | 30 | 1.1 | 2.3 | 3 | 70.5 |

*1 Average particle size here is defined as average particle size obtained by laser diffraction method. The median diameter of the particle based on volume corresponds to 50% of cumulative distribution. This was determined by a laser diffraction type particle size distribution measuring system (Horiba Ltd.: LA-500).
*2 Specific volume is defined as a volume occupied by an object having unit mass. To determine this, the specimen is dried at constant temperature of 105°, and it is placed gently into a graduated test tube having volume of 20 ml. This test tube is placed in a metal tube and cover is put on it. By dropping this from a height of 45 mm by 400 times at the frequency of one time per 2 seconds. Then, the volume is read, and specific volume is obtained by the following equation:
Specific volume (ml/g) = Volume (ml)/3 (g)
*3 To determine this value, the specimen synthetic mica powder is coated on adhesive surface of cellotape attached on a piece of art paper, and glossiness at 60°–60° was determined by a portable digital glossimeter (Nippon Den-shoku Kogyo Co., Ltd.; VG-2PD).

(EXAMPLE 30)

Paint

The pearlescent pigment of the present invention as obtained in Example 1 was mixed by about 10 weight % with thermosetting acrylmelamine resin (Dainippon Ink Co., Ltd.; a mixture of Acryldic 47-712 and Superbeckamine G821-60 by weight ratio of 7:3). This was sprayed on a steel plate undercoated with black enamel (Nippon Paint Co., Ltd.; Superlack F-47). Top clear of the thermosetting acrylmelamine resin (Dainippon Ink Co., Ltd.; a mixture of Acryldic 44-179 and Superbeckamine L117-60 by weight ratio of 7:3) was sprayed on it on wet-on-wet basis. This was baked at 140° for 18 minutes.

The coated film showed golden interference pearl luster and had high chroma, luminosity and interference property.

(EXAMPLE 31)

Plastics

Four parts of the pearlescent pigment of the present invention as obtained in Example 1 were mixed with about 100 parts of vinyl chloride resin, 40 parts of dioctyl phthalate, and 3 parts of zinc stearate. The mixture was processed for 3 minutes using twin-roll mill heated to 165° C., thus molding into a sheet of 0.5 mm thick.

As a result, a vinyl chloride sheet was obtained, which showed golden color and interference pearl luster in semi-transparent reflection light.

(EXAMPLE 32)

Cosmetic Material (Lipstick)

A lipstick was prepared from the following materials at the following composition:

| | |
| --- | --- |
| Pigment prepared in Example 1 | 15 parts |
| Red pigment No. 226 | 1 part |
| Perfume | 0.5 part |
| Lipstick base material | 83.5 parts |

The above lipstick base material was prepared by blending the following substances;

| | |
| --- | --- |
| Beeswax | 15 parts |
| Cetyl alcohol | 3 parts |
| Lanolin | 15 parts |
| Castor oil | 62 parts |
| Liquid paraffin | 5 parts |

The lipstick thus produced showed golden color with clear pearl-like gloss.

(EXAMPLE 33)

Cosmetic Material (Foundation Cream)

| | |
| --- | --- |
| Pigment prepared in Example 3 | 20 parts |
| Liquid paraffin | 25 parts |
| Vaseline | 5 parts |
| Isopropyl myristate | 5 parts |
| Stearic acid | 2 parts |
| POE (25) monostearate | 2 parts |
| Yellow oxide | 2 parts |
| Blood red | 1 part |
| Talc | 5 parts |
| Propyleneglycol | 5 parts |
| Glycerine | 5 parts |
| Perfume | 0.5 part |
| Purified water | 22.5 parts |

The above materials were evenly dissolved and mixed at 75° to 80° C., and the mixture was then cooled to 30° C. to prepare the product.

This product had high color clearness and was highly ductile. For this reason, it is suitable for easier cosmetic make-up, and the makeup is not easily removed.

(EXAMPLE 34)

Ink

To 100 parts of rotogravure ink medium, 15 parts of the pigment prepared in Example 1 was added. After mixing well, gravure pearl ink was prepared.

When this ink was used for printing, the printed paper showed golden interference color with elegant interference pearl luster and superb feeling.

(EXAMPLE 35)

Paint

The pearlescent pigment of the present invention as prepared in Example 21 was mixed by about 10 weight % with thermosetting acrylmelamine resin (a mixture of Acryldic 47-712 and Superbeckamine G821-60 by weight ratio of 7:3; Dainippon Ink Co., Ltd.). This was sprayed on a steel plate undercoated with black enamel (Nippon Paint Co., Ltd.; Superlack F-47). The top clear of the thermosetting acrylmelamine resin (Dainippon Ink Co., Ltd.; A mixture of Acryldic 44-179 and Superbeckamine L117-60 by weight ratio of 7:3) was sprayed on it on wet-on-wet basis, and this was baked at 140° C. for 18 minutes.

The coated film thus prepared showed golden color and had high chroma, luminosity and interference property with interference pearl luster.

(EXAMPLE 36)

Plastics

Four parts of the pearlescent pigment of the present invention prepared in Example 21, about 100 parts of vinyl chloride resin, 40 parts of dioctyl phthalate, and 3 parts of zinc stearate were mixed by processing for 3 minutes using twin-roll mill heated to 165° C., thus molding into a sheet of 0.5 mm thick.

As a result, elegant vinyl chloride sheet having golden color with semitransparent reflection light and with interference pearl luster was obtained.

(EXAMPLE 37)

Cosmetic Material (Lipstick)

A lipstick was produced from the following materials at the composition indicated:

| | |
|---|---|
| Pigment prepared in Example 21 | 15 parts |
| Red pigment No. 226 | 1 part |
| Perfume | 0.5 part |
| Lipstick base material | 83.5 parts |

The above lipstick base material was prepared by blending the following substances:

| | |
|---|---|
| Beeswax | 15 parts |
| Cetyl alcohol | 3 parts |
| Lanolin | 15 parts |
| Castor oil | 62 parts |
| Liquid paraffin | 5 parts |

The lipstick thus produced showed golden color with clear pearl-like luster.

(EXAMPLE 38)

Cosmetic Material (Foundation Cream)

| | |
|---|---|
| Pigment prepared in Example 23 | 20 parts |
| Liquid paraffin | 25 parts |
| Vaseline | 5 parts |
| Isopropyl myristate | 5 parts |
| Stearic acid | 1 part |
| POE (25) monostearate | 2 parts |
| Yellow oxide | 2 parts |
| Blood red | 1 part |
| Talc | 5 parts |
| Propyleneglycol | 5 parts |
| Glycerine | 5 parts |
| Perfume | 0.5 part |
| Purified water | 22.5 parts |

The above materials were evenly dissolved and mixed at 75° to 80° C., and this was cooled down to 30° C. to prepare the foundation cream.

This foundation cream had high color clearness and was highly ductile. For this reason, it is suitable for easier cosmetic make-up, and the makeup is not easily removed.

(EXAMPLE 39)

Ink

To 100 parts of rotogravure ink medium, 15 parts of the pigment prepared in Example 21 were added. After mixing well, gravure pearl ink was prepared.

When this ink was used for printing, the printed paper showed golden interference color with elegant rainbow-colored pearl-like luster and superb feeling.

As described above, it is possible according to the present invention to eliminate problems such as disappearance of color tone specific to mica at mass tone angle or shade side and whiting and non-clear undertone color when painted due to stronger interference effect because Fe content of the synthetic mica (average refractive index not higher than 1.58) is limited to not more than 1.0%. As a result, brightness and color clearness of the pearlescent pigment are extensively improved, and remarkable brightness as not found in the conventional type pearlescent pigment is achieved. Thus, the pigment is very useful as the new luster pigment for paint, plastics, ink, or cosmetic products. By making the end thickness thinner than the center thickness in the pearlescent pigment, the influence of irregular reflection on end surface can be avoided. This makes it possible to provide a pearlescent pigment, which shows brightness and color clearness not seen in the conventional type pearlescent pigment. By limiting Fe content to not more than 0.1%, by smoothing the mica surface without processing through heat treatment, and by using synthetic mica having pearl parameter of more than 10, brightness and color clearness can be extensively improved.

What we claim are:

1. A pearlescent pigment, comprising a synthetic mica coated with a metal oxide, whereby average refractive index of said synthetic mica is not more than 1.58, surface of synthetic mica particles is smoothed and made flaky, the synthetic mica contains iron in not more than 0.1 weight %, and said synthetic mica has a pearl parameter given by the following equation:

Pearl parameter=Specific volume $(A)$×Powder luster value $(B)$≧10.

2. A pearlescent pigment according to claim 1, wherein pearl parameter of said synthetic mica is expressed by the following equation:

30≧Pearl parameter=Specific volume $(A)$×Powder luster value $(B)$≧10.

3. A pearlescent pigment according to claim 1, wherein thickness of said pearlescent pigment is adjusted in such manner that thickness at central portion is higher than the thickness at end surface.

4. A pearlescent pigment according to claim 2, wherein thickness of said pearlescent pigment is adjusted in such manner that thickness at central portion is higher than the thickness at end surface.

5. A pearlescent pigment according to claim 3, wherein a ratio of thickness at end surface to thickness at central portion of said pearlescent pigment is not higher than 0.9.

6. A pearlescent pigment according to claim 4, wherein a ratio of thickness at end surface to thickness at central portion of said pearlescent pigment is not higher than 0.9.

7. A pearlescent pigment according to claim 1, wherein said synthetic mica is a synthetic fluoro phlogopite.

8. A pearlescent pigment according to claim 2, wherein said synthetic mica is a synthetic fluoro phlogopite.

9. A pearlescent pigment according to claim 1, wherein said synthetic mica is produced by pulverizing easily flakable crystal mass and consists of flaky particles with smooth surface.

10. A pearlescent pigment according to claim 2, wherein said synthetic mica is produced by pulverizing easily flakable crystal mass and consists of flaky particles with smooth surface.

11. A pearlescent pigment according to claim 1, wherein, to produce said synthetic mica, synthetic mica raw material is melted by internal resistance electric melting method, a perforation is bored in the melting shell, a melted substance taken out through the perforation is crystallized in a heat insulating case, and crystallized mass is then pulverized to prepare synthetic mica powder.

12. A pearlescent pigment according to claim 2, wherein, to produce said synthetic mica, synthetic mica raw material is melted by internal resistance electric melting method, a perforation is bored in the melting shell, a melted substance taken out through the perforation is crystallized in a heat insulating case, and crystallized mass is then pulverized to prepare synthetic mica powder.

13. A pearlescent pigment according to claim 1, wherein average aspect ratio of said synthetic mica is 60 or more.

14. A pearlescent pigment according to claim 2, wherein average aspect ratio of said synthetic mica is 60 or more.

15. A pearlescent pigment according to claim 1, wherein said synthetic mica has average particle diameter of plane direction of 3 to 100 µm and thickness of 0.5 to 1 µm.

16. A pearlescent pigment according to claim 2, wherein said synthetic mica has average particle diameter of plane direction of 3 to 100 µm and thickness of 0.5 to 1 µm.

17. A pearlescent pigment according to claim 1, wherein said metal oxide is an oxide of titanium, zirconium, iron, chromium, or vanadium.

18. A pearlescent pigment according to claim 2, wherein said metal oxide is an oxide of titanium, zirconium, iron, chromium, or vanadium.

19. A pearlescent pigment according to claim 17, wherein said metal oxide is rutilized.

20. A pearlescent pigment according to claim 19, wherein said metal oxide is titanium dioxide, and said titanium dioxide is rutilized.

21. A paint composition, comprising a pearlescent pigment coated with a metal oxide on a synthetic mica, said synthetic mica has average refractive index of not more than 1.58, and surface of synthetic mica particles is smoothened and made flaky, and iron content in the synthetic mica is not higher than 1.0%.

22. A cosmetic material, comprising a pearlescent pigment coated with a metal oxide on a synthetic mica, said synthetic mica has average refractive index of not more than 1.58, surface of synthetic mica particles is smoothened and made flaky, and iron content in the synthetic mica is not higher than 1.0%.

23. An ink, comprising a pearlescent pigment coated with a metal oxide on a synthetic mica, said synthetic mica has average refractive index of not more than 1.58, surface of synthetic mica particles is smoothened and made flaky, and iron content in the synthetic mica is not higher than 1.0%.

24. A plastic material, comprising a pearlescent pigment coated with a metal oxide on a synthetic mica, said synthetic mica has average refractive index of not more than 1.58, surface of synthetic mica particles is smoothened and made flaky, and iron content in the synthetic mica is not higher than 1.0%.

* * * * *